US009504488B2

(12) United States Patent
Fallin et al.

(10) Patent No.: US 9,504,488 B2
(45) Date of Patent: Nov. 29, 2016

(54) MEANS OF DIRECT VISUALIZATION THROUGH A CURVED APPROACH PATH

(75) Inventors: T. Wade Fallin, Hyde Park, UT (US); Douglas M. Lorang, North Logan, UT (US); Ephraim Akyuz, Providence, UT (US)

(73) Assignee: Innovative Spine, LLC., Clovis, CA (US)

( * ) Notice: Subject to any disclaimer, the term of this patent is extended or adjusted under 35 U.S.C. 154(b) by 386 days.

(21) Appl. No.: 12/692,747

(22) Filed: Jan. 25, 2010

(65) Prior Publication Data

US 2010/0210917 A1    Aug. 19, 2010

Related U.S. Application Data

(60) Provisional application No. 61/146,976, filed on Jan. 23, 2009.

(51) Int. Cl.
| | |
|---|---|
| *A61B 1/32* | (2006.01) |
| *A61B 17/34* | (2006.01) |
| *A61B 17/02* | (2006.01) |
| *A61B 1/313* | (2006.01) |
| *A61B 17/00* | (2006.01) |

(52) U.S. Cl.
CPC ........... *A61B 17/3421* (2013.01); *A61B 17/02* (2013.01); *A61B 1/3135* (2013.01); *A61B 2017/00477* (2013.01); *A61B 2017/0256* (2013.01); *A61B 2017/3447* (2013.01)

(58) Field of Classification Search
CPC ...... A61B 1/32; A61B 1/313; A61B 1/3132; A61B 1/317; A61B 17/02
USPC ........... 606/90, 99, 86 A, 105; 600/184–246
See application file for complete search history.

(56) References Cited

U.S. PATENT DOCUMENTS

| | | | | |
|---|---|---|---|---|
| 4,982,729 | A * | 1/1991 | Wu ................................ 600/187 |
| 6,174,282 | B1 * | 1/2001 | Tan .............................. 600/224 |
| 8,636,654 | B2 * | 1/2014 | Protopsaltis ............. A61B 1/32 |
| | | | | 600/201 |
| 2007/0027364 | A1 * | 2/2007 | Schwer ............. A61B 17/0206 |
| | | | | 600/219 |
| 2009/0099605 | A1 * | 4/2009 | Fallin ................ A61B 17/7085 |
| | | | | 606/252 |
| 2009/0131755 | A1 * | 5/2009 | White .................... A61B 17/02 |
| | | | | 600/210 |

* cited by examiner

*Primary Examiner* — Ellen C Hammond
*Assistant Examiner* — Christina Negrellirodrigue
(74) *Attorney, Agent, or Firm* — GSS Law Group

(57) ABSTRACT

A coupled pair of retractors which are coupled at the distal end to allow the handles at the proximal end to be urged apart to increase the distance between handles to allow for direct line of sight to the surgical site while also allowing the use of curved tools and curved access to the surgical site. A cannula with a cross section taken perpendicular to a straight portion of the cannula that increases between the proximal end of the cannula and the distal end of the cannula allows for direct line of sight to the surgical site while also allowing the use of curved tools and curved access to the surgical site. These tools may be used in a postero-lateral approach from an incision in the back to a target position adjacent to the spine.

2 Claims, 5 Drawing Sheets

MEANS OF DIRECT VISUALIZATION THROUGH A CURVED APPROACH PATH

CROSS-REFERENCE TO RELATED APPLICATIONS

This application is part of a series of applications addressing tools and methods used in a postero-lateral approach from an incision in the back to a target position adjacent to the spine. One recent filing in this sequence is U.S. application Ser. No. 12/537,941 filed Aug. 7, 2009 for Surgical Access with Target Visualization. The '941 application provides useful information on the anatomy and related information that helps provide context for some uses of the material disclosed in this application.

This application claims priority to U.S. Provisional Patent Application No. 61/146,976 for Means of Direct Visualization Through a Curved Approach Path.

The above-identified documents are incorporated herein by reference. While these applications have been incorporated by reference to provide additional detail it should be noted that these other applications were written at an earlier time and may have had a different focus from the present application. Thus, to the extent that the teachings or use of terminology differ in any of these incorporated applications from the present application, the present application controls.

BACKGROUND

Field of the Disclosure

This disclosure relates generally to orthopedics, and more particularly, to systems and methods for providing access to the spine to facilitate various therapies.

SUMMARY OF THE DISCLOSURE

A system for accessing a spine from a curved postero-lateral approach may include an access route through either a special cannula or a coupled pair of retractors along a curved path from an opening in the skin to a location proximate the spine. An interbody device may be implanted into an intervertebral space through this curved path. Work on the surgical site is facilitated by tools that allow for direct visualization of the surgical site.

This summary is meant to introduce the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features, and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The figures provide a framework for discussing the various teachings of the present disclosure and are not intended to provide an exhaustive set of templates of the various ways that teachings of the present disclosure may be used. The components in the figures are not necessarily to scale, emphasis instead being placed upon illustrating the principles of the disclosure. Moreover, in the figures, like reference numerals designate corresponding parts throughout the different views.

DETAILED DESCRIPTION

Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts in the appended claims.

The present disclosure may be used as part of a process to access the spine through the use of postero-lateral approaches. Postero-lateral approaches may have significant advantages in spinal orthopedic procedures over the lateral and anterior approaches. These advantages may include avoiding the need to turn the patient during surgery, less muscle refraction, less blood loss, less operating room time, minimized damage to the vascular system, organs, nerves and muscles, faster recovery, and an improved overall outcome for the patient.

Figure 1:
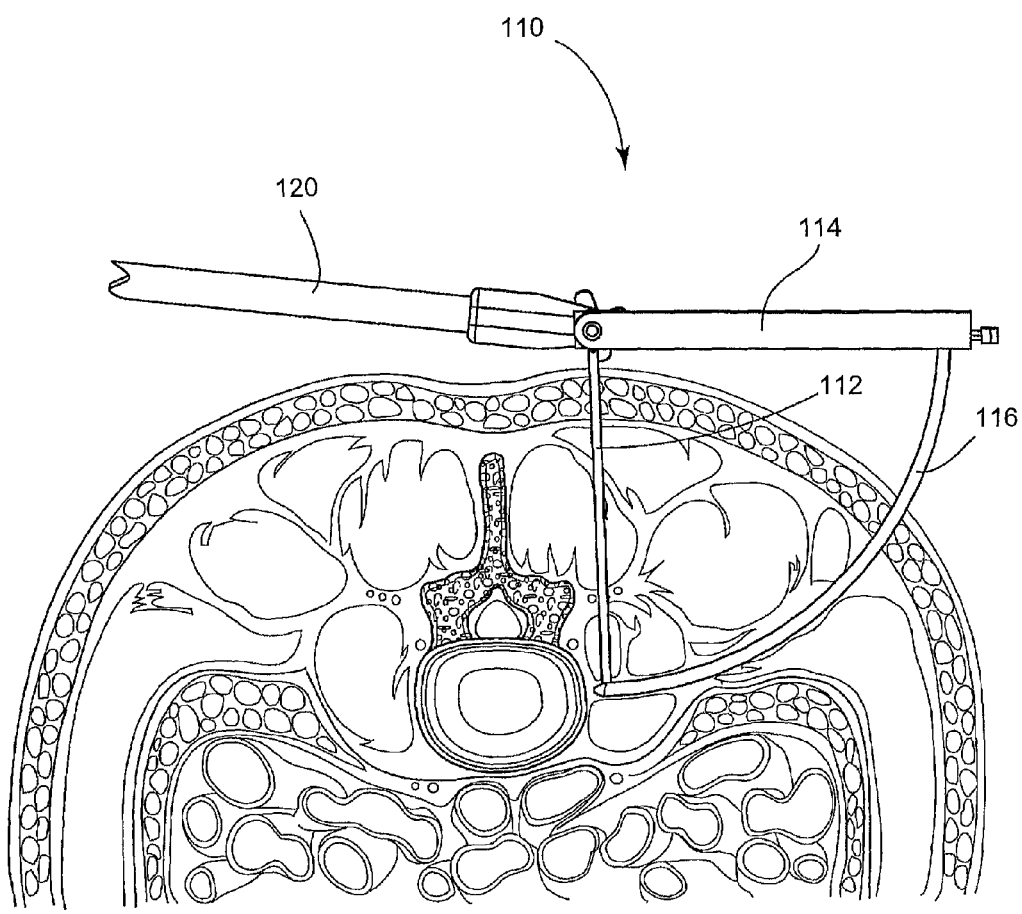
FIG. 1 is a cephalad view of a cross-section of a portion of a patient with an arcuate cannula assembly deployed adjacent a portion of the spine.

Referring to FIG. 1, one embodiment of an arcuate cannula assembly 110 is shown. The assembly 110 includes a targeting post 112, a guide arm 114, and a curved penetrating guide member 116 (for short-simply guide member 116). An instrument support arm 120 holds the assembly 110 and connects to an operating table (not shown). The assembly 110 may further comprise a series of graduated curved cannulas (not shown in FIG. 1), which are introduced sequentially over the guide member 116 to create access to a targeted portion of a spine. Use of the arcuate cannula assembly 110 creates an access portal to the intervertebral disc space or any element of the anterior spinal column through an arcuate path, from a postero-lateral approach.

The access portal is an unimpeded passage through which surgical instruments, implants and other materials may be passed to complete a variety of intervertebral procedures. This arcuate postero-lateral approach may be advantageous in performing a number of procedures, including but not limited to: implantation of motion preservation devices, total disc replacement, implantation of interbody devices, discectomy, lateral plating with or without dynamic elements, vertebra fixation or graft compression using plates or staples, foraminotomy, decompression, annulotomy, nucleotomy, annulus or nucleus repair, vertebral body biopsy, vertebroplasty, height restoration of a collapsed vertebral body (vertebral body augmentation), implantation of a fusion cage with stabilization features, implantation of a fusion cage with teeth to hold endplates together, implantation of a curved or straight staple across the disc space to provide compression on the cage and stabilization of the cage, or other therapies known in the art and adapted for the postero-lateral access route.

Combination of Tissue Retractors.

Tissue retractors of a number of types are known in the art. The present disclosure teaches that a pair of tissue refractors may be combined together. The possible combinations include:

An anterior retractor combined with a posterior retractor;
An anterior retractor combined with a straight retractor; and
A straight retractor combined with a posterior retractor.

Anterior and posterior retractors may be substantially identical except for orientation of a curve (anteriorly or posteriorly oriented) and placement of the handles or coupling features.

Figure 2:
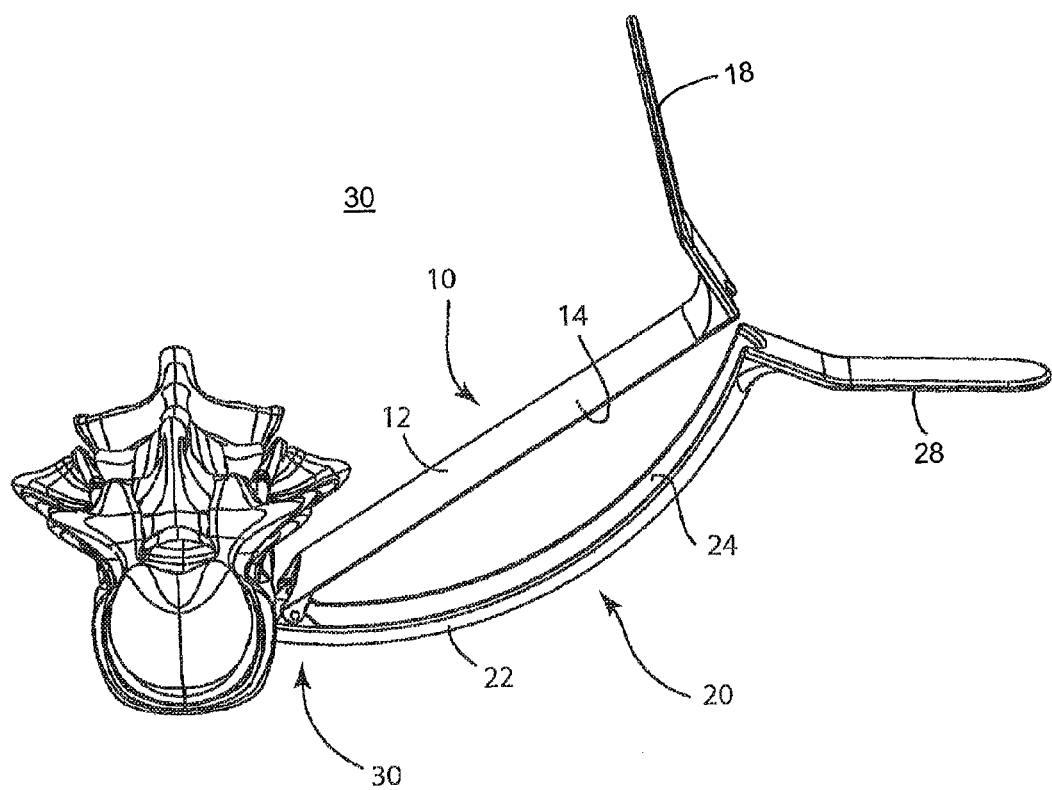
FIG. 2 is a side view of a coupled retractor pair adjacent to a surgical site in a spine, with the coupled retractor pair substantially closed.
Figure 3:
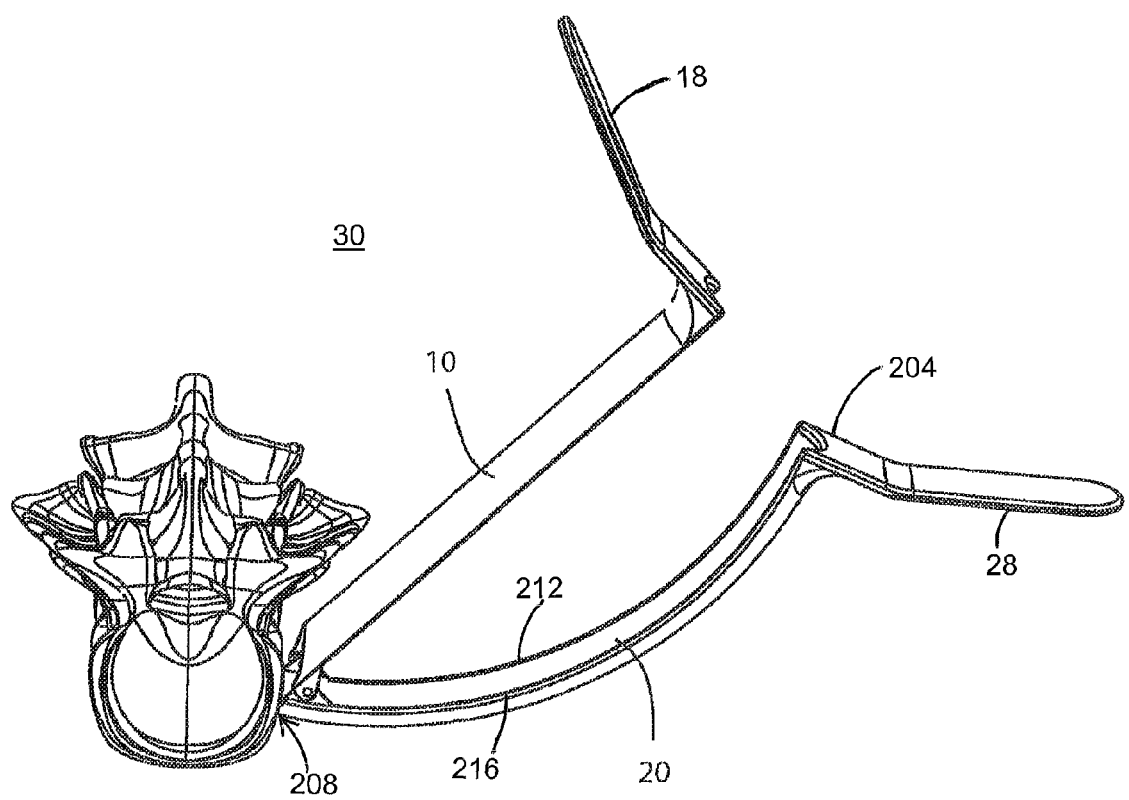
FIG. 3 is a side view of a coupled retractor pair adjacent to a surgical site in a spine, with the coupled retractor pair substantially opened relative to FIG. 2.

FIG. 2 and FIG. 3 show a coupled retractor pair with a curved anterior retractor coupled to a straight retractor with pivoting connections at the distal tip. Ideally, the pivoting connection does not substantially obstruct a delivery path out the distal end of the coupled refractor pair to the adjacent surgical site. The coupled retractor pair allows tissue to be retracted to gain direct visualization of the distal tip of the coupled retractor pair and to the tissue adjacent to the distal tip.

The refractors may be inserted from a postero-lateral approach from an incision in the patient's back to a target position adjacent the spine. The target position may be an intervertebral location.

FIG. 2 shows a straight retractor 10 and a curved retractor 20 joined at their distal ends by coupling feature 30 to form coupled retractor pair 30. FIG. 2 shows the coupled refractor pair 30 in a substantially closed position with the handles 18 and 28 relatively close to one another.

FIG. 3 in contrast shows the coupled retractor pair 30 in a partially open position with handles 18 and 28 separated by a greater distance than shown in FIG. 2. After urging the handles 18 and 28 to separate as shown in FIG. 3, the viewing area between retractors has been enlarged. The position shown in FIG. 3 may allow more room for insertion of instruments between the retractors. For example, instruments may be inserted between retractors into the intervertebral area to:

Perform a discectomy
Implant a fusion device or
Perform some other therapy or procedure.

With the coupled retractor pair 30 positioned as shown in FIG. 3, a direct line of sight from the proximal end of a retractor to the distal end of the retractors may be possible.

As illustrated in FIG. 2 and FIG. 3, each retractor may also be curved across its width. Thus as shown in FIG. 3 curved retractor 20 is curved between proximal end 204 and distal end 208 along the long axis if the refractor. Curved retractor 20 is also curved between right side 212 and left side 216. Retractor 10 is not curved along its length but is curved along its width. As noted in FIG. 2, straight retractor 10 has a convexly curved outer surface 12 and a concavely curved inner surface 14. Similarly, curved retractor 20 has a convexly curved outer surface 22 and a concavely curved inner surface 24. Retractors may be used that are not curved across the inner or outer surfaces. One of skill in the art will recognize that connecting a flat (not curved side to side) retractor at the pivot point may require having a pair of protrusions for use in the pivot.

Another viable combination of retractors is a curved anterior retractor coupled to a curved posterior retractor in a manner analogous to that shown in FIG. 2 and FIG. 3. Yet another viable combination is a curved posterior retractor coupled to a straight retractor. The difference from the coupled retractor pair 30 in FIG. 2 and FIG. 3 is that the curve of the refractor would be oriented posteriorly rather than anteriorly.

Snap-on Coupling.

The retractors do not have to be permanently attached to one another. The coupling feature may be a snap-on feature that would allow each retractor to remain a separate component which may be inserted separately including one retractor at a time. Once positioned within the body, the retractors may be coupled using a snap coupling. Once coupled at the distal end, the handles at the proximal end could be urged apart. The movement of the handles of the coupled refractor pair would cause the movement of tissue to afford a direct line of sight to the surgical site at the distal end of the coupled retractors.

Cannulas with Variable Cross Sections.

Figure 4:
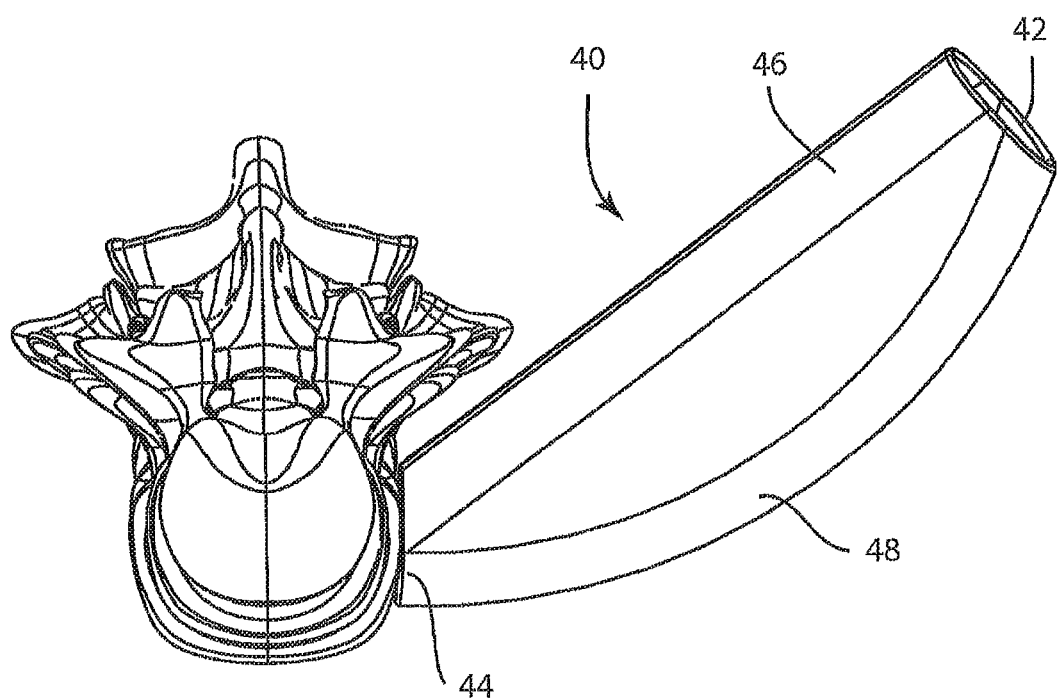
FIG. 4 is a side view of cannula 40 adjacent to a surgical site in a spine.
Figure 5:
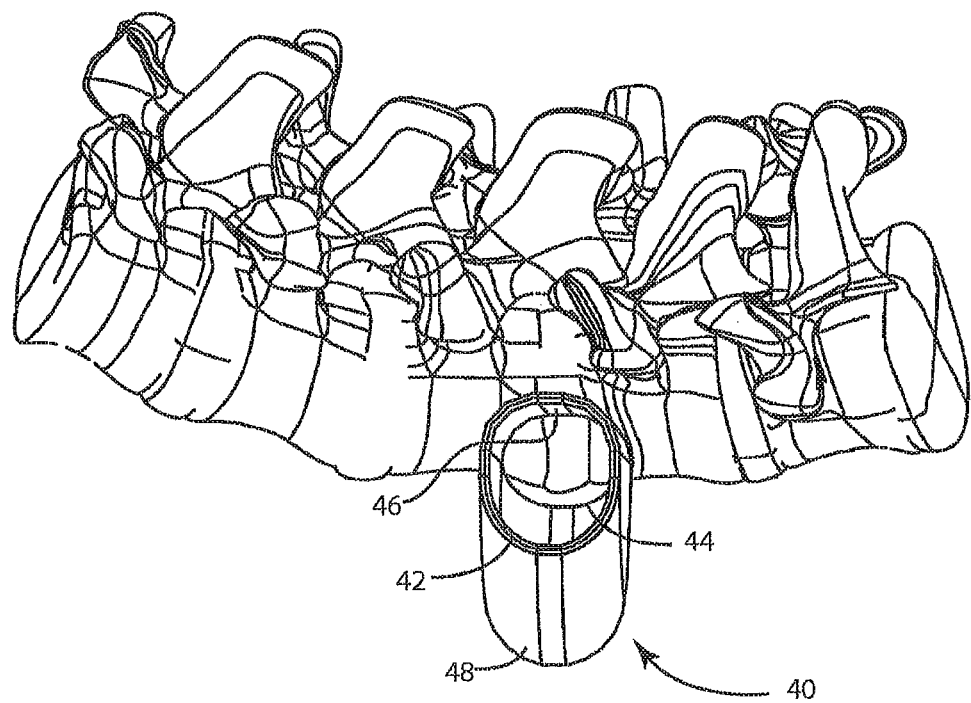
FIG. 5 is a view of the surgical site through the proximal end of cannula 40.

FIG. 4 and FIG. 5 provide two views of a cannula 40. Cannula 40 provides a direct line of sight to a surgical site at the distal end of the cannula while allowing the use of curved tools that provide a curved access to the surgical site and thus allow lateral access of the site though a posterior entry site into the patient's body. Cannula 40 can be thought of as a hybrid of an anterior retractor combined with a straight retractor.

Cannula 40 has proximal end 42 and distal end 44. A substantially straight portion 46 extends from the proximal end 42 to distal end 44. A curved portion 48 extends from proximal end 42 to distal end 44. As the straight portion 46 and curved portion 48 are joined at each end but do not have the same rate of curvature between the proximal and distal ends, the cross section of the cannula 40 changes from the proximal end 42 to distal end 44 with the greatest cross section found partway between the proximal end 42 and distal end 44. Cross section in this context is taken perpendicular to straight portion 46.

The cannula 40 may be of one-piece construction or may be made from two or more pieces that are coupled together.

General Comments.

The cannulas and retractors disclosed in this application may comprise radiolucent materials such as aluminum or rigid plastic materials.

Any cannula or retractor disclosed in this application may be connected to an EMG or similar system for nerve tissue monitoring as the cannula or retractor is inserted.

Any cannula or retractor disclosed in this application may be adapted with connection features to permit attachment to operating tables or other instruments.

Systems for lighting or visualization may be inserted into the cannulas or between the refractors to provide additional light or ways to provide enhanced visualization of the surgical site. The systems may include lasers, mirrors, light sources, fiber optics, endoscopes, and other visualization means known in the art.

The present disclosure may be embodied in other specific forms without departing from its spirit or essential characteristics. For example, above are described various alternative examples of systems for accessing intervertebral space. It is appreciated that various features of the above-described examples can be mixed and matched to form a variety of other alternatives. It is also appreciated that this system should not be limited to creating access to the intervertebral space. The tools set forth above may be used to obtain access to any portion of the spine or for access to other parts of the body. As such, the described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A cannula for use in surgery, the cannula comprising:
    a first cannula section having a proximal end, a distal end, a right side, a left side, an inner side;
    a second cannula section having a proximal end, a distal end, a right side, a left side, an inner side;
    a proximal connection located at the proximal end of the first cannula section and the proximal end of the second cannula section and connecting the proximal end of the first cannula section to the proximal end of the second cannula section;
    a distal connection located at the distal end of the first cannula section and the distal end of the second cannula section and connecting the distal end of the first cannula section to the distal end of the second cannula section;
    a first curvature pattern between the proximal end of the first cannula section and the distal end of the first cannula section;
    and a second curvature pattern between the proximal end of the second cannula section and the distal end of the second cannula section, wherein the first curvature pattern is not equal to the second curvature pattern so the distance between the inner side of the first cannula section to the inner side of the second cannula section is not constant,
    wherein the distance between the inner side of the first cannula section to the inner side of the second cannula section is greatest at a location partway between the proximal ends of the first cannula section and the second cannula section and the distal ends of the first cannula section and the second cannula section.

2. The cannula of 1, wherein the first curvature pattern is a lack of curvature and this is a straight line between the proximal end of the first cannula section and the distal end of the first cannula section.

* * * * *